United States Patent
Ishizuka et al.

(10) Patent No.: US 7,432,071 B2
(45) Date of Patent: Oct. 7, 2008

(54) METHOD OF DIAGNOSING PERIODONTITIS BY DETERMINING γ-GLUTAMYLTRANSPEPTIDASE

(75) Inventors: Yasuyuki Ishizuka, Kawasaki (JP); Shunpei Niida, Oobu (JP)

(73) Assignee: Applyed Cell Biotechnologies Inc., Tsukuba-shi (JP)

( * ) Notice: Subject to any disclaimer, the term of this patent is extended or adjusted under 35 U.S.C. 154(b) by 217 days.

(21) Appl. No.: 10/561,967

(22) PCT Filed: Jun. 28, 2004

(86) PCT No.: PCT/JP2004/009117

§ 371 (c)(1),
(2), (4) Date: May 8, 2006

(87) PCT Pub. No.: WO2005/001484

PCT Pub. Date: Jan. 6, 2005

(65) Prior Publication Data

US 2006/0228768 A1    Oct. 12, 2006

(30) Foreign Application Priority Data

Jun. 30, 2003    (JP) .............................. 2003-188247

(51) Int. Cl.
*C12Q 1/37*    (2006.01)

(52) U.S. Cl. ....................................................... 435/24

(58) Field of Classification Search ..................... 435/24
See application file for complete search history.

(56) References Cited

U.S. PATENT DOCUMENTS 4,981,787 A * 1/1991 Baram ......................... 435/16

FOREIGN PATENT DOCUMENTS

| EP | 0 158 796 | | 10/1985 |
| JP | 60-222768 | | 11/1985 |
| JP | 4229198 | * | 12/1990 |
| JP | 3-501447 | | 4/1991 |
| JP | 4-229198 | * | 8/1992 |
| JP | 5-176796 | | 7/1993 |
| JP | 2004/129584 A | * | 10/2002 |
| WO | WO 2004/033716 A1 | * | 4/2004 |

OTHER PUBLICATIONS

Brenda Name Document 2008 for GTP.*

* cited by examiner

*Primary Examiner*—Ralph Gitomer
(74) *Attorney, Agent, or Firm*—Birch, Stewart, Kolasch & Birch, LLP

(57) ABSTRACT

The inventor discovered that γ-GTP (γ-glutamyl transpeptidase) was scarcely contained in the gingival crevicular fluid of patients with gingivitis, but was contained in the gingival crevicular fluid of patients with periodontitis. Thus, the inventor provides a determination method of development of periodontitis by detecting or measuring γ-GTP contained in the gingival crevicular fluid. Also, this method can be applied to the determination of the development of peri-implant inflammation.

20 Claims, 1 Drawing Sheet

METHOD OF DIAGNOSING PERIODONTITIS BY DETERMINING γ-GLUTAMYLTRANSPEPTIDASE

This application is a National Stage filed under Rule 371 based on PCT/JP04/09117 filed Jun. 28, 2004 which claims priority to Japan 2003 188247 filed Jun. 30, 2003.

TECHNICAL FIELD

The present invention relates to method of judging the onset of periodontitis and peri-implant periodontitis. More specifically, the present invention relates to method of judging the onset of periodontitis and peri-implant periodontitis, characterized by the detection or measurement of γ-GTP (γ-glutamyl transpeptidase) activity.

BACKGROUND ART

The periodontium is the tissue that surrounds and supports teeth, consisting of the gingiva, periodontal membrane, cementum, and alveolar bone. Among periodontal inflammations, inflammation limited to the gingiva is called "gingivitis," and inflammation whose lesion spreads beyond the gingiva to damage and destroy the periodontal membrane and alveolar bone is called "periodontitis."

Both gingivitis and periodontitis are periodontal inflammations caused by bacterial growth in plaque (intraoral mass of food residue and others, where bacteria adhere and grow) and other factors. However, in the case of gingivitis, gingival inflammation does not spread to the periodontal membrane and alveolar bone and thus can be treated by intraoral cleaning, but when gingivitis advances to periodontitis, a tooth becomes loose, and the periodontal membrane and alveolar bone are damaged and destroyed, with resulting difficulties in fixation even though intraoral cleaning is carried out.

Diagnosis of periodontal diseases is generally conducted by measurement of a periodontal pocket, attachment level, X-ray diagnosis, and others. A "periodontal pocket" is a crevice (a gingival crevice) between the tooth and gingiva, caused by gingival detachment from tooth due to gingivitis or periodontitis; thus, the severity of destruction of the periodontium can be known to some extent by measuring the depth of a periodontal pocket. "Attachment level" is a distance from the boundary between the cementum and enamel to the bottom of a periodontal pocket, an indicator to know the severity of the destruction of periodontal supporting tissue. In "X-ray diagnosis," absorption of the alveolar bone and others can be observed by radiography.

Several diagnostic methods of periodontal diseases using measurement of various enzymes contained in the fluid leaked out into the said gingival crevice (gingival crevicular fluid) during gingivitis and periodontitis have been proposed. For example, a diagnostic method of periodontal diseases, which measures peroxidase activity elevated along with increased leukocytes during inflammation, has been disclosed (patent document 1).

In addition, a diagnostic method of periodontal diseases, which measures ALT (alanine aminotransferase) concentration that is increased in gingival crevicular fluid due to periodontal inflammation and damage, has been disclosed (patent document 2).

Also, there is prior literature concerning an objective diagnostic method of the advancement stages of periodontal diseases by specifically detecting ALP (alkaline phosphatase) enzymes released by pathogenic bacteria of periodontal diseases such as *Bacteroides gingivalis* (patent document 3). In this method, ALP collected from saliva and others is heat-treated to remove ALP derived from the patient's cells; thus, only bacteria-derived ALP is specifically measured.

Patent document 1: Japanese Published Unexamined Patent Application No. S60-222768

Patent document 2: Japanese Translation of International Application (Kohyo) No. H3-501447

Patent document 3: Japanese Published Unexamined Patent Application No. H5-176796

DISCLOSURE OF THE INVENTION

Problems to be Solved by the Invention

However, the conventional techniques had the following problems to be solved.

When gingival inflammation is found through inspection and others, there have been common problems that a great deal of experience and skill have been required to make a distinction between gingivitis and periodontitis, and that a distinct diagnosis of gingivitis and periodontitis is extremely difficult to make. In addition, a distinction between gingivitis and periodontitis is usually made based upon a dentist's experience and skill; thus, there has been a problem that dentists' criteria vary between individuals. The conventional diagnostic methods of periodontal disease, which measure various enzymes, also have problems such as the difficulty in making a clear distinction between gingivitis and periodontitis, complexity of operational procedures, insufficient sensitivity, and necessity of skills.

For example, in the invention of the patent document 1, the severity of periodontal inflammation is determined by measuring the increased enzyme activity of peroxidase, but the enzyme activity of peroxidase is increased in both gingivitis and periodontitis; thus, it is difficult to make a clear distinction between gingivitis and periodontitis.

In the invention of the patent document 2, periodontal inflammation and damage are determined by measuring the increased ALT concentration, but the enzyme activity of ALT is increased in both gingivitis and periodontitis as described above; thus, it is difficult to make a clear distinction between gingivitis and periodontitis, even if the advancement of symptoms of periodontal disease can be predicted to some extent.

Also, in the invention of the patent document 3, enzymes released from the pathogenic bacteria of periodontal diseases are used as a marker; thus, the advancement of periodontal diseases may be predicted to some extent, but it is difficult to make a clear distinction between gingivitis and periodontitis. In addition, since the relationship between the advancement of periodontal diseases and bacterial growth varies between individuals, it is difficult to make a clear distinction between gingivitis and periodontitis in each patient, even if the measured values of enzymes released from bacteria are the same in several patients.

As described above, the conventional methods have a problem that a clear distinction between gingivitis and periodontitis cannot be made easily. Early detection and rapid cure are needed when gingivitis advances to periodontitis; thus, a method to make a clear distinction between gingivitis and periodontitis and determine the development of periodontitis has been needed. Therefore, the principal aim of the present invention is to provide a simple method to make a clear distinction between gingivitis and periodontitis.

Means of Solving the Problems

To solve the above technical problem, the following means are provided in the present invention.

First, γ-GTP (γ-glutamyl transpeptidase), an enzyme related to the present invention, is abundant in the kidneys, pancreas, liver, and others, and is leaked out into the blood during increased alcohol metabolism and jaundice and thus is used for the diagnosis of liver diseases and others.

Recently, the present inventor has newly discovered that γ-GTP is not contained in the gingival crevicular fluid of patients who developed gingivitis, but is contained in the gingival crevicular fluid of patients who developed periodontitis via gingivitis. Besides this discovery, the inventor has also confirmed that osteoclasts are recruited to the periodontium when γ-GTP is expressed in the periodontium. These new findings demonstrate that γ-GTP is deeply involved in the development of periodontitis accompanied by absorption and destruction of the alveolar bone. At the time that γ-GTP is contained in gingival crevicular fluid, osteoclasts are being recruited to the periodontium; thus, absorption and destruction of the alveolar bone are not yet initiated, but are just beginning, periodontitis is considered to be in its early stage.

Thus, γ-GTP is a useful marker to make a distinction between gingivitis and periodontitis, and detection and measurement of γ-GTP in gingival crevicular fluid can determine if gingivitis is advancing to periodontitis.

Therefore, based on the said discoveries, the present invention provides method of judging the onset of periodontitis by detecting or measuring γ-GTP (γ-glutamyl transpeptidase) contained in gingival crevicular fluid.

As described above, γ-GTP is scarcely contained in the gingival crevicular fluid during gingivitis, but leaks out into gingival crevicular fluid during periodontitis; thus, detection or measurement of γ-GTP in gingival crevicular fluid can clearly determine whether the periodontal disease is gingivitis, and whether the periodontal disease is advancing to periodontitis. Here, the "gingival crevice" indicates a crevice between the tooth and gingiva (periodontal pocket), formed by their detachment due to gingival inflammation. In addition, "gingival crevicular fluid" indicates tissue fluid leaked out into the gingival crevice. A gingival crevice is formed by gingival inflammation, and there are few distinct gingival sulci (periodontal pockets) in a healthy periodontium; thus, little gingival crevicular fluid can be collected.

Methods to collect gingival crevicular fluid include, for instance, those by soaking fluid into a paper point, using a sucker or micropipette (capillary), and by washing the gingival crevice with a buffer.

The heretofore known methods that are routinely used in the laboratory diagnosis of liver diseases and others can be used to detect or measure γ-GTP, and there is no methodological limitation as long as γ-GTP can be detected or measured. For instance, a method to measure γ-GTP enzyme activity, a direct quantification method using anti-γ-GTP antibody, and a gene detection method to confirm expression of mRNA coding for γ-GTP by a PCR method can be used.

To detect or measure the enzyme activity of γ-GTP using an enzyme activity assay, the recommended method described previously (see Rinshokagaku, 24, 106-121, 1995), for instance, can be used. γ-GTP is a transferase with an activity to produce L-γ-glutamyl glycylglycine and 5-amino-2-nitrobenzoic acid by transferring γ-glucosyl of the donor substrate, L-γ-glutamyl-3-carboxy-4-nitroanilide, to a receptor substrate, glycylglycine. In the recommended method, the change of the absorbance of 5-amino-2-nitrobenzoic acid produced in this reaction is measured to detect and measure enzyme activity of γ-GTP. In addition, a similar method that uses a synthetic substrate L-γ-glutamyl-p-nitroanilide (SSCC method) can also be used as a method to detect and measure enzyme activity by reacting γ-GTP with a substrate.

The direct quantification method directly detects and measures γ-GTP using anti-γ-GTP antibody (antibody that specifically binds to γ-GTP). For instance, a commonly-used sandwich ELISA (enzyme-linked immunosorbent assay) can be used to detect γ-GTP with high sensitivity.

In addition, the present invention can also be applied to the determination method of the development of peri-implant inflammation.

"Peri-implant inflammation" is a kind of periodontitis, inflammation around the periodontium, caused by an implant buried in the periodontium. An "implant" is a base buried in the periodontium; a denture is fixed by burying the lower part of the implant in the periodontium and fixing the upper part to the denture. Peri-implant inflammation is a new periodontitis, increasing with the widespread use of dental implants, and does not develop via advancement of gingivitis, thus being characterized in that periodontal pockets are not necessarily the predominant symptom during the development of peri-odontitis.

Since peri-implant inflammation does not develop via the advancement of gingivitis, it is usually difficult to confirm and determine its development by inspection or enzyme activity. γ-GTP is not associated with gingivitis, and is leaked out into gingival crevicular fluid, tissue fluid, and periodontal blood only during periodontitis (absorption of the alveolar bone and others); thus, peri-implant inflammation can be easily determined with it.

Since periodontal pockets are not necessarily the predominant symptom of peri-implant inflammation, gingival crevicular fluid cannot be collected sufficiently in some patients. In such cases, blood around the implanted region is collected with a syringe, and can be used as a sample to detect and measure γ-GTP. Since gingival crevicular fluid is lymph fluid leaked out from the gingiva due to inflammation, its component is much the same as a serum component; thus, γ-GTP can be detected and measured by blood sampling. The same method as described above can be used to detect and measure γ-GTP.

EXAMPLES

Example 1

In Example 1, gingival crevicular fluid was collected to measure the enzyme activity of γ-GTP, and an experiment to make a distinction between gingivitis and periodontitis was performed according to the following procedures. The present invention is not limited to the examples.

First, gingival crevicular fluid was respectively collected from 3 patients (a patient with previously-cured periodontitis, a patient with gingivitis, and a patient with periodontitis). Gingival crevicular fluid was collected by inserting a paper point into the gingival crevice of the patient to soak up gingival crevicular fluid for a minute. In the patient with previously-cured periodontitis, gingival crevicular fluid was respectively collected from 2 sites: a gingival crevice with a shallow periodontal pocket and a gingival crevice with a deep periodontal pocket on another site. In the patient with periodontitis, gingival crevicular fluid was respectively collected from 3 sites: the presently inflamed gingival crevice (periodontal pocket), a gingival crevice with a shallow periodontal pocket in a site where gingival inflammation was suppressed, and a gingival crevice with a deep periodontal pocket on another site where gingival inflammation was suppressed.

Next, the paper point that soaked up gingival crevicular fluid was collected and immediately immersed in a 70 μL PBS buffer (or distilled water) to prevent drying of the tip of the paper point (a part inserted into the periodontal pocket) Then, after discarding the paper point, only the PBS buffer, in which the paper point was immersed for a minute, was stored at 4° C. In this procedure, the tip of the paper point, which soaked up gingival crevicular fluid, can be cut and left immersed in the PBS buffer to be stored at 4° C.

The reason why the PBS buffer, into which gingival crevicular fluid was eluted, was stored at 4° C. is that γ-GTP may be degraded by proteases secreted by bacteria, contaminated and grown in the gingival crevicular fluid, at room temperature. To solve this problem, 0.1% BSA (to stabilize traces of γ-GTP) and 0.2% sodium azide (preservative) can be added to the PBS buffer. By taking one of the above procedures, γ-GTP samples can be stored and transported without being degraded at 4° C. (low temperature) or room temperature. The above procedures are required mainly for storage and transportation of samples. Thus, when samples can be used immediately for measurement of γ-GTP, they do not need to be stored at 4° C.

Then, the activity of γ-GTP contained in the PBS buffer, into which gingival crevicular fluid was eluted, was measured by an enzyme activity assay. The results are shown in FIG. 1.

TABLE 1

| Sample | γ-GTP activity (IU/L) | Characteristics of samples |
|---|---|---|
| 1 | 0 | Patient without present periodontal inflammation |
| 2 | 0 | Patient without present periodontal inflammation (Patient with a deep periodontal pocket) |
| 3 | 0 | Patient with gingivitis (not periodontitis) |
| 4 | 3.92 | Patient with periodontitis |
| 5 | 3.62 | Patient with suppressed periodontitis |
| 6 | 4.07 | Patient with suppressed periodontitis (Patient with a deep periodontal pocket) |

γ-GTP was not detected in the gingival crevicular fluid collected from both the shallow and deep gingival sulci (periodontal pockets) of patients whose gingivitis or periodontitis was suppressed by treatment (Samples 1 and 2).

γ-GTP was not detected in the gingival crevicular fluid collected from the patient with gingivitis (Sample 3), either, but was detected in the gingival crevicular fluid collected from the patient with periodontitis (Sample 4). Thus, it was demonstrated that a clear distinction between gingivitis and periodontitis could be made by detecting and measuring γ-GTP. γ-GTP was not contained in the gingival crevicular fluid of the patient with gingivitis, but was contained in the gingival crevicular fluid of the patient with periodontitis.

In samples 5 and 6, γ-GTP contained in gingival crevicular fluid was measured in patients whose periodontitis was suppressed by the use of an antiinflammatory agent (steroid drug and others). The use of antiinflammatory agent suppressed the gingival inflammation on the surface (redness), but in fact, periodontitis was not cured, and inflammation remained in the deep portion of the periodontium. Thus, this experiment examined whether the present invention could determine the presence of inflammation in the deep portion of the periodontium. As a result, as shown in FIG. 1, γ-GTP was detected in patients of samples 5 and 6. Thus, it has been demonstrated that the present invention can determine the presence of periodontitis when it seemingly is cured by the use of an antiinflammatory agent on the surface but the inflammation remains in the deep portion of the periodontium.

In addition, when samples 5 and 6 were compared, the enzyme activity of γ-GTP was higher in the gingival crevicular fluid collected from the deep gingival crevice (periodontal pocket) (Sample 5) than from the shallow gingival crevice (periodontal pocket) (Sample 6). This indicates that the closer the gingival crevice is to the site of inflammation, the more abundant γ-GTP is, and that the larger the inflammation is, the more abundant γ-GTP is when gingival crevicular fluid is collected at the same depth of the gingival sulci. Thus, it has been demonstrated that the present invention can determine the severity of periodontal inflammation when a diagnosis of periodontitis is made, as well as make a distinction between gingivitis and periodontitis.

Example 2

Example 2 is an experiment to determine γ-GTP mRNA expression in the gingival crevicular fluid, prepared from patients with periodontal diseases, using a gene detection method.

First, RNA was extracted from the gingival crevicular fluid of patients with a periodontal disease using the RNA extraction reagent ISOGEN (NIPPON GENE Co., Ltd). Next, DNA of interest was synthesized and amplified by a RT-PCR method using a RT-PCR high-Plus-kit (TOYOBO). Primers used in the RT-PCR method were as follows: 5'-TCCCT-TGACCTTCAGGAGAACGAG-3' and 5'-GTGTGGTGCT-GTTGTAGATGGTGA-3'. As a result, the DNA of interest was amplified by the PCR method using these primers, demonstrating the human γ-GTP mRNA expression in the gingival crevicular fluid.

The above results suggested that γ-GTP in gingival crevicular fluid could be detected also by a gene detection method.

Example 3

Example 3 is an experiment that indicates the involvement of γ-GTP in the destruction of the alveolar bone using rat models with experimental periodontal disease. The procedures are described below.

Seven-week-old Wistar rats were fixed under anesthesia, and occluding right and left molars were exposed to LPS for an hour. Then, they were euthanized on day 0, 1, 2, 3, and 7, and the periodontium was collected and formalin-fixed, according to the standard method, to prepare pathological sections. "LPS" is lipopolysaccharide, an important component of the outer membrane of gram-negative bacteria. LPS has various biological activities as endotoxin, and thus was used to develop experimental periodontitis by sensitizing rat molars via exposure to LPS for a certain period of time in this experiment. *E. coli* LPS was used.

First, the pathological sections were stained with γ-GTP (FIG. 1). And pathological sections prepared in the same manner, stained with a non-specific antibody, were prepared as a control (FIG. 2). As observed in FIG. 1, the results showed large amounts of γ-GTP expression around the alveolar bone of rats with experimental periodontitis. FIG. 1 and FIG. 2 show pathological sections stained on day 3 after LPS sensitization.

Next, the pathological sections, prepared in the same manner, were TRAP-stained (FIG. 3). TRAP staining is a method that uses tartrate-resistant acid phosphatase (mature osteoclast marker), and can specifically stain osteoclasts. As a result, many osteoclasts were found to be recruited to the alveolar bone of rats with experimental periodontitis. FIG. 3 shows pathological sections stained on day 3 after LPS sensitization. In the observation by optical microscope, recruitment of osteoclasts was observed in the pathological sections on day 3 after LPS sensitization, but absorption and destruction of the alveolar bone was rarely observed.

The above experiments demonstrated the high expression of γ-GTP in the periodontium during gingivitis. In addition, osteoclasts were found to be recruited to the alveolar bone along with the γ-GTP expression. Thus, it was demonstrated that γ-GTP was expressed during gingivitis, recruited osteoclasts to the alveolar bone, and was involved in the absorption and destruction of the alveolar bone. In addition, γ-GTP was found to be already expressed immediately before the absorption and destruction of the alveolar bone actually began.

The effects provided by the present invention are as follows.

A clear distinction between gingivitis and periodontitis can be made by a simple method. In addition, clear criteria for distinction between gingivitis and periodontitis can be set; thus, development of periodontitis can be determined based on not a dentist's individual criteria but objective criteria. This can be useful in early diagnosis and early treatment of periodontitis. In particular, γ-GTP expression begins immediately before the absorption and destruction of the alveolar bone and thereby is useful also in the early diagnosis of periodontitis.

The heretofore known simple method used in the laboratory diagnosis of liver diseases and others can be used to detect and measure γ-GTP. Thus, the method of the present invention can be popularized readily and rapidly.

By detecting and measuring γ-GTP, an enzyme involved in the development of periodontitis, a direct distinction between gingivitis and periodontitis can be made, and the development of periodontitis can be determined. In particular, the present invention uses neither an enzyme involved in periodontal inflammation and damage nor an enzyme released by bacteria that causes periodontal diseases, but uses an enzyme directly related to the development of periodontal diseases as a marker to determine the development of periodontitis; thus, distinction between gingivitis and periodontitis, and determination of the development of periodontitis can be made clearly and reliably.

In patients with periodontitis, gingival inflammation (redness) is seemingly cured on the surface by the use of an antiinflammatory agent, but in fact, the inflammation is not cured in the deep portion of the periodontium; thus, discontinuation of treatment at that time may only exacerbate the periodontitis. The method of the present invention can readily and accurately determine whether the inflammation in the deep portion of the periodontium is actually cured in patients who are taking an antiinflammatory agent.

The present invention cannot only make a distinction between gingivitis and periodontitis, but also determine the size of inflammation of periodontitis by measuring γ-GTP when periodontitis is determined.

The present invention is also useful in determining the development of peri-implant inflammation.

Figure 1:
FIG. 1 is a substitute picture for the drawing of rat alveolar bone on day 3 after LPS sensitization, stained with γ-GTP antibody.
Figure 2:
FIG. 2 is a substitute picture for the drawing of rat alveolar bone on day 3 after LPS sensitization, stained with non-specific antibody.
Figure 3:
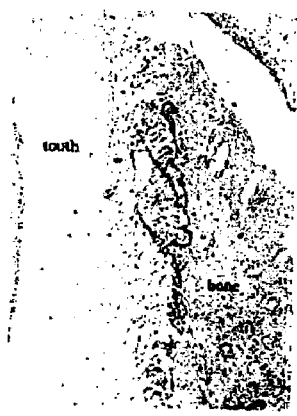
FIG. 3 is a substitute picture for the drawing of TRAP-stained rat alveolar bone on day 3 after LPS sensitization.

What is claimed is:

1. A method of diagnosing periodontitis, comprising:
    testing gingival crevicular fluid for the presence of γ-glutamyltranspeptidase;
    wherein detection of γ-glutamyltranspeptidase is indicative of a patient with periodontitis.

2. A method of diagnosing peri-implant inflammation, comprising:
    testing blood collected around an implant whose base is buried in the periodontium for the presence of γ-glutamyltranspeptidase;
    wherein detection of γ-glutamyltranspeptidase is indicative of a patient with peri-implant inflammation.

3. The method of claim 1, wherein said gingival crevicular fluid is collected before being tested.

4. The method of claim 2, wherein said blood is collected before being tested.

5. The method of claim 3, wherein said gingival crevicular fluid is collected by soaking fluid into a paper point, using a sucker or micropipette (capillary), and/or by washing the gingival crevice with a buffer.

6. The method of claim 4, wherein said blood is collected before being tested by soaking fluid into a paper point, using a sucker or micropipette (capillary), and/or by washing the gingival crevice with a buffer.

7. The method of claim 5, wherein said testing is conducted by measuring γ-glutamyltranspeptidase activity.

8. The method of claim 6, wherein said testing is conducted by measuring γ-glutamyltranspeptidase activity.

9. The method of claim 5, wherein said testing is conducted by measuring γ-glutamyltranspeptidase mRNA expression.

10. The method of claim 6, wherein said testing is conducted by measuring γ-glutamyltranspeptidase mRNA expression.

11. The method of claim 5, wherein said testing is conducted by contacting with an antibody specific for γ-glutamyltranspeptidase.

12. The method of claim 6, wherein said testing is conducted by contacting with an antibody specific for γ-glutamyltranspeptidase.

13. The method of claim 3, wherein said patient does not have periodontal inflammation.

14. The method of claim 3, wherein said patient does not have periodontal inflammation but has a deep periodontal pocket.

15. The method of claim 3, wherein said patient has gingivitis.

16. The method of claim 15, wherein a positive test for γ-glutamyltranspeptidase indicates that said patient also has periodontitis.

17. The method of claim 4, wherein said patient does not have periodontal inflammation.

18. The method of claim 4, wherein said patient does not have periodontal inflammation but has a deep periodontal pocket.

19. The method of claim 4, wherein said patient has gingivitis.

20. The method of claim 19, wherein a positive test for γ-glutamyltranspeptidase indicates that said patient also has periodontitis.

* * * * *